(12) United States Patent
Eaton

(10) Patent No.: US 6,315,796 B1
(45) Date of Patent: Nov. 13, 2001

(54) FLEXIBLE SEAMLESS MEMORY TISSUE EXPANDING IMPLANT

(75) Inventor: L. Daniel Eaton, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/311,825

(22) Filed: May 13, 1999

(51) Int. Cl.[7] .................................. A61F 2/12; A61F 2/04

(52) U.S. Cl. ........................................... 623/8; 623/23.67

(58) Field of Search .................... 623/7, 8, 23.67, 623/23.68, 23.71; 604/43

(56) References Cited

U.S. PATENT DOCUMENTS

| | | |
|---|---|---|
| 2,580,264 | 12/1951 | Wright et al. . |
| 3,366,975 | 2/1968 | Pangman . |
| 3,845,507 | 11/1974 | Kirby et al. . |
| 3,860,969 | 1/1975 | Arion . |
| 3,897,376 | 7/1975 | Lampe . |
| 3,905,376 | 9/1975 | Johnson et al. . |
| 3,925,277 | 12/1975 | Lampe . |
| 4,086,666 | 5/1978 | Vaskys . |
| 4,253,201 | 3/1981 | Ross et al. . |
| 4,263,682 | 4/1981 | Bejarno . |
| 4,364,880 | 12/1982 | Howse . |
| 4,401,492 | 8/1983 | Pfrommer . |
| 4,428,364 * | 1/1984 | Bartolo .............................. 623/7 X |
| 4,546,899 | 10/1985 | Williams . |
| 4,574,780 | 3/1986 | Manders . |
| 4,643,733 | 2/1987 | Becker . |
| 4,668,567 | 5/1987 | Williams . |
| 4,671,255 * | 6/1987 | Dubrul et al. . |
| 4,676,795 | 6/1987 | Grundei . |
| 4,681,587 | 7/1987 | Eberl et al. . |
| 4,731,081 | 3/1988 | Tiffany et al. . |
| 4,826,501 * | 5/1989 | Grundei . |
| 4,841,992 | 6/1989 | Sasaki et al. . |
| 4,863,477 | 9/1989 | Monson . |
| 4,899,764 | 2/1990 | Gauger et al. . |
| 4,902,294 | 2/1990 | Gossarez . |
| 4,944,749 | 7/1990 | Becker . |
| 4,995,882 | 2/1991 | Destouet et al. . |
| 5,005,591 | 4/1991 | Austad . |

(List continued on next page.)

FOREIGN PATENT DOCUMENTS

| | | | |
|---|---|---|---|
| 4115428 | 11/1992 | (DE) . | |
| 0 422 302 A1 * | 4/1991 | (EP) | ........................................ 623/8 |
| 0 469 165 A1 * | 2/1992 | (EP) | ........................................ 623/8 |
| 2202745 | 10/1988 | (GB) . | |

Primary Examiner—David H. Willse
(74) Attorney, Agent, or Firm—Ray F. Cox, Jr.

(57) ABSTRACT

A flexible, seamless tissue expanding implant with predetermined memory shape to augment tissue for accurate anatomical restoration for alloplastic reconstruction. The implant is a hollow shape formed from a material that tends to resume its molded shape even when collapsed and when reinflated resumes the desired shape. A minimal incision is made in the patient. From the incision a pocket is formed under the skin of the patient. The pocket is sized to hold the implant, which is inserted, in a collapsed deflated condition. The incision is then closed and allowed to heal. The implant is provided with a one-way, self-sealing valve for periodic inflation. The one-way valve is a latex plug encapsulated with silastic and incorporated into the implant. The valve can be palpated by the surgeon so that inflation can be performed with the implant in place by inserting a hypodermic needle through the skin of the patient, through the valve and into the interior of the implant. The implant is injected with the filling material at periodic intervals so that the tissue is gradually expanded to the appropriate extent. Since the implant has previously been formed into the desired shape, the implant gradually assumes the predetermined shape as it is filled. Therefore, the tissue likewise assumes the desired shape and predetermined volume augmenting the deficient anatomy predictably.

5 Claims, 2 Drawing Sheets

U.S. PATENT DOCUMENTS

| | | |
|---|---|---|
| 5,019,101 | 5/1991 | Purkait et al. . |
| 5,035,249 | 7/1991 | Sasaki et al. . |
| 5,035,758 | 7/1991 | Degler et al. . |
| 5,091,121 | 2/1992 | Nakada et al. . |
| 5,133,753 | 7/1992 | Bark et al. . |
| 5,236,454 * | 8/1993 | Miller ........................................ 623/8 |
| 5,282,856 | 2/1994 | Ledergerber . |
| 5,308,420 | 5/1994 | Yang . |
| 5,352,307 | 10/1994 | Wild . |
| 5,358,521 | 10/1994 | Shane . |
| 5,376,323 | 12/1994 | Eaton . |
| 5,496,367 | 3/1996 | Fisher . |
| 5,496,370 | 3/1996 | Hamas . |
| 5,527,359 | 6/1996 | Nakamura et al. . |
| 5,558,829 * | 9/1996 | Petrick ................................. 264/263 |
| 5,607,473 | 3/1997 | Weber-Unger et al. . |
| 5,632,777 | 5/1997 | Petrick . |
| 5,645,597 | 7/1997 | Krapiva . |
| 5,658,329 | 8/1997 | Purkait . |
| 5,658,330 | 8/1997 | Carlisle et al. . |
| 5,700,288 | 12/1997 | Eaton . |
| 5,702,454 | 12/1997 | Baumgartner . |
| 5,855,606 | 1/1999 | Eaton . |

* cited by examiner

FLEXIBLE SEAMLESS MEMORY TISSUE EXPANDING IMPLANT

BACKGROUND OF THE INVENTION

The present invention relates to a tissue expanding implant, and in particular, to a tissue expanding implant having a predetermined shape memory so that the implant will tend to reassume the predetermined shape after being collapsed and reinflated.

Tissue expanders are valuable in various surgical procedures where tissues must be expanded, particularly where tissues must be expanded to accommodate a prosthetic implant. Tissue expanders generally comprise flexible fluid-tight envelopes that are inserted subcutaneously into the portion of the patient's anatomy requiring augmentation. The tissue expander is inserted in a collapsed state. Various means are then employed to gradually inflate the tissue expander with a suitable fluid until the tissue expander, and thus the overlying tissue, expands to the desired extent. The means of inflating the tissue expander include tubes leading from the interior of the tissue expander to the exterior of the patient's body and the direct injection of fluid from a hypodermic needle through the patient's skin into the interior of the tissue expander. Once the tissue expander has been inflated to the desired extent, the tissue expander must normally be removed surgically from the patient and the actual prosthesis inserted.

Tissue expanders can be as simple as elastic balloons which expand when inflated in the same manner as balloons; i.e., substantially equally in all directions. It is desirable however that the tissue be expanded in accordance with the anatomical feature being replicated. A breast prosthesis implant, for example, should resemble a natural breast. The overlying tissue therefore is desirably expanded into complex shapes not easily achievable with simple elastic balloons. Numerous attempts have been made to achieve tissue expanders which are able to achieve complex shapes that more nearly replicate the shape of the desired tissue augmentation that is required to produce results that are anatomically satisfying.

One such solution is found in U.S. Pat. Nos. 5,035,249; 4,481,992 and 4,899,764, which disclose a tissue expander comprising a fluid tight envelope having portions with varying degrees of elasticity. The tissue expander is inflated and the varying degrees of elasticity control the amount of expansion of each portion and therefore the final shape of the tissue expander.

U.S. Pat. No. 4,574,780 discloses a tissue expander formed of a silicone elastomer such as Silastic® (Dow Corning). The tissue expander comprises a liquid impervious chamber with walls having a thickness that decreases from one end to the other. Expansion of the chamber by injection with fluid such as saline causes the thinner portions of the wall to expand to a greater extent that the thicker portions, thus allowing for differential expansion of the device.

In addition to the problem of achieving complex shapes of tissue augmentation suitable for implanted prostheses that replicate natural anatomy, there is the problem of injecting the fluid to gradually inflate the tissue expander. To avoid having tubes and the like penetrating the skin of the patient, it is desirable for the inflation to be accomplished by hypodermic needles through the skin of the patient and thence into the interior of the tissue expander. The elastic envelopes of tissue expanders, however, are typically not self-sealing and may be prone to undesirable leakage if penetrated by a hypodermic needle. The usual solution is to provide a self-sealing valve through which the hypodermic needle can penetrate without the risk of leakage.

U.S. Pat. No. 5,019,101 discloses a self-sealing valve for an implantable device. The valve includes a body with a channel which has an unevenly stressed section wherein the unevenly stressed section folds back to occlude the channel when a fill tube is withdrawn. The valve also includes a gel-filled chamber that occludes the end of the channel when the fill tube has been withdrawn.

U.S. Pat. No. 4,671,255 discloses a tissue expander comprising a silicone rubber cover attached to a base. A self-sealing injection reservoir is protected by a reinforcing member substantially more rigid that the expandable shell to prevent the folding of the expandable shell over the injection reservoir to prevent inadvertent puncturing of the expandable shell by a hypodermic needle.

It is known that latex rubber is self-sealing from a hypodermic needle puncture. This property has been employed in stoppers of drug vials. A hypodermic needle punctures the latex rubber stopper and withdraws fluids from the bottle. When the needle is withdrawn the puncture seals to avoid the loss of the remaining contents of the vial.

U.S. Pat. No. 5,005,951 avoids the problem of inflating the tissue expander. It discloses a self-inflating tissue expander comprising an envelope portion constructed of a material that is substantially impervious to body fluids. A window is attached to the envelope which is permeable to body fluids. An osmotic agent is disposed within the envelope and induces an osmotic differential across the window that draws body fluids into the envelope and thereby expands the envelope. A rigid base may be provided to limit expansion in particular directions.

The limitations of the prior art are overcome by the present invention as described below.

SUMMARY OF THE INVENTION

The present invention is a flexible, seamless tissue expanding implant with predetermined memory shape to augment tissue for appropriate and accurate anatomical restoration for alloplastic reconstruction; e.g., head and neck, thorax, etc. The implant is a hollow shape formed preferably from room temperature vulcanizable (RTV) silicone, such as Silastic® medical adhesive silicone Type A (Dow Corning) using, e.g., the method disclosed in U.S. Pat. No. 5,376,323, which is incorporated herein by reference. The implant is formed so that when inflated it assumes the desired shape. For example, when the implant is to be used to replace a surgically removed breast, the implant is desirably formed into a mirror image of the remaining natural breast. However, the device is not limited to breast reconstruction and may be used in any situation requiring alloplastic reconstruction following ablative trauma or surgical disfiguration.

According to the method of the present invention, a minimal incision is made in the patient. From the incision a pocket is formed under the skin of the patient. The pocket is sized to hold the implant that is inserted in a collapsed deflated condition. The incision is then closed and allowed to heal.

The implant is provided with a one-way, self-sealing valve for periodic inflation with air and/or a triglyceride oil, such as soybean oil or rice oil. Saline may also be employed to inflate the implant. Soybean oil is more desirable than saline since soybean oil is less dense than saline but more viscous. The result is a lighter and more naturally behaving filling material. In the preferred embodiment, the one-way valve is a latex plug encapsulated with silicone and incorporated into the silicone implant. The valve can be palpated by the surgeon so that inflation can be performed with the implant in place by inserting a hypodermic needle through the skin of the patient, through the valve and into the interior of the implant. The implant is injected with the filling material at periodic intervals so that the tissue is gradually expanded to the appropriate extent. Since the implant has previously been formed into the desired shape, the memory inherent in the pre-formed shape of the implant allows the implant to gradually assume the predetermined shape as it is filled. Therefore, the tissue likewise assumes the desired shape and predetermined volume augmenting the deficient anatomy predictably.

The prior art techniques are not predictable. The present invention is also less invasive requiring only a small incision and a one stage operation, since an expander does not have to be removed and the implant has a predetermined shape. The present invention could be used for mid-face augmentation following neoplastic surgery or trauma. The present invention is particularly applicable to mastectomy patients. The present invention saves tissue and allows for a precise tissue size, shape and contour for plastic reconstruction.

It is therefore an object of the present invention to provide for a tissue expander formed into the desired final shape of the tissue, and in particular, to a tissue expander formed from a material having the properties of assuming the desired shape upon being filled with a suitable fluid.

These and other objects and advantages of the present invention will be apparent from a consideration of the following detailed description of the preferred embodiments in conjunction with the appended drawings as described following.

DETAILED DESCRIPTION OF THE PREFERRED EMBODIMENTS

With reference to FIGS. 1–4, the preferred embodiment of the present invention may be described. The present invention is a flexible, seamless tissue expanding implant with predetermined memory shape to augment tissue for appropriate and accurate anatomical restoration for alloplastic reconstruction. The invention may be particularly useful in the restoration of deficient anatomy in the head, neck and thorax, but is not specifically limited thereto.

Figure 2:
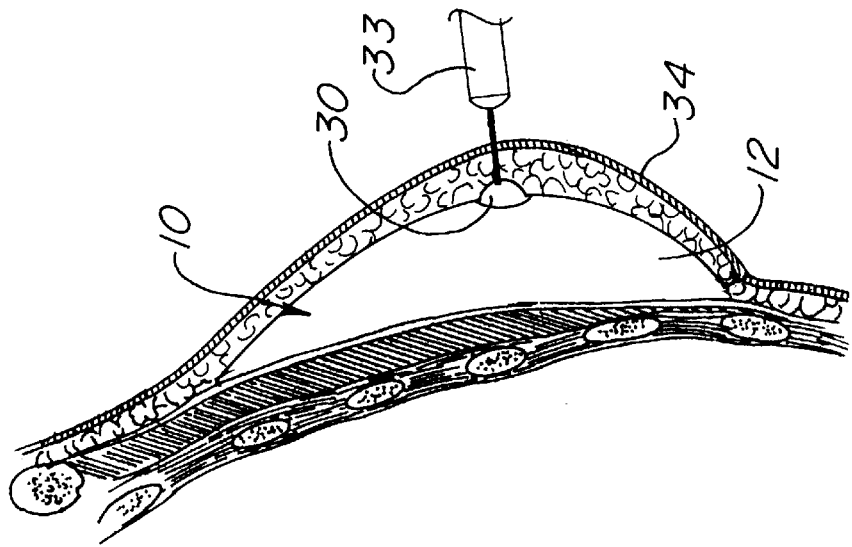
FIG. 2 is a sectional elevational view of the embodiment of FIG. 1 showing a hypodermic needle penetrating the skin of the patient and through the self-sealing valve into the interior of the tissue expander.
Figure 1:
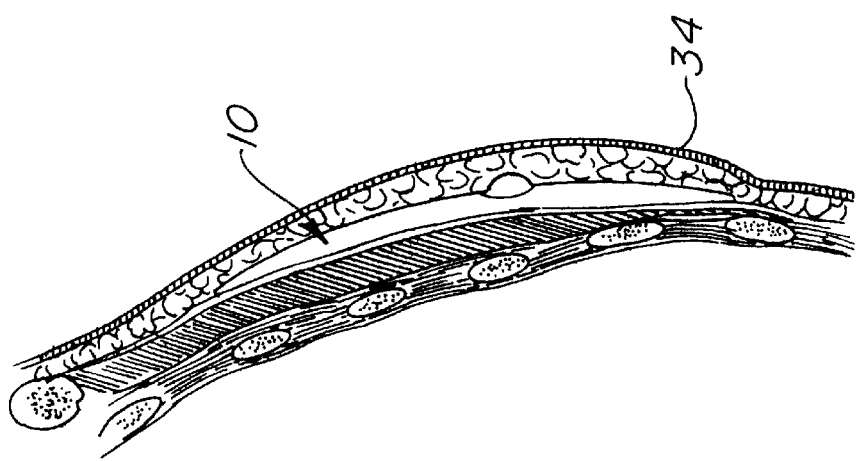
FIG. 1 is a sectional elevational view of an embodiment of the present invention for augmenting tissue for replacing a breast lost due to mastectomy and the like. The tissue expander is shown in a collapsed state immediately after insertion under the skin of the patient.
Figure 4:
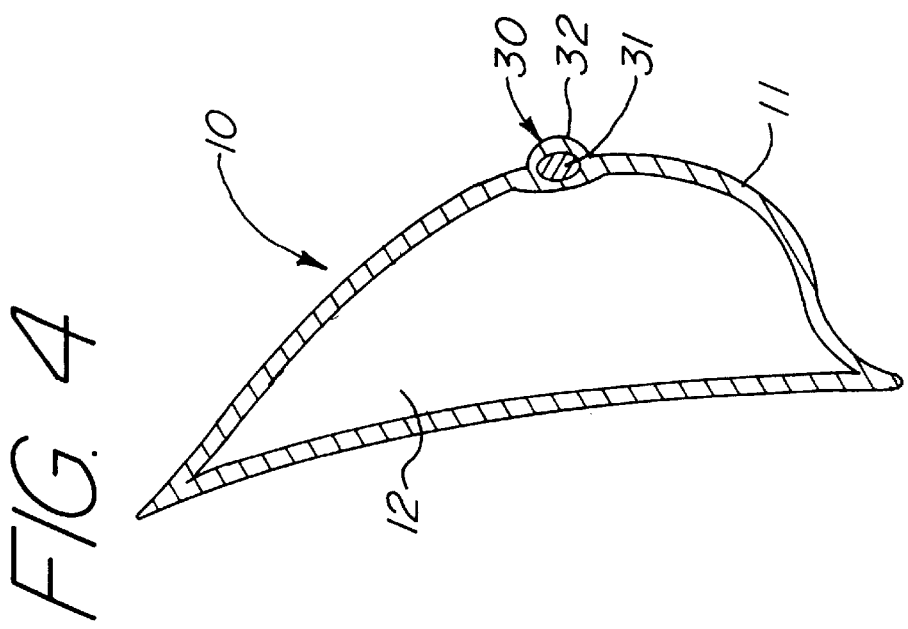
FIG. 4 is a sectional elevational view of the tissue expander as removed from the mold before being collapsed and inserted into a pocket beneath the skin of the patient.
Figure 3:
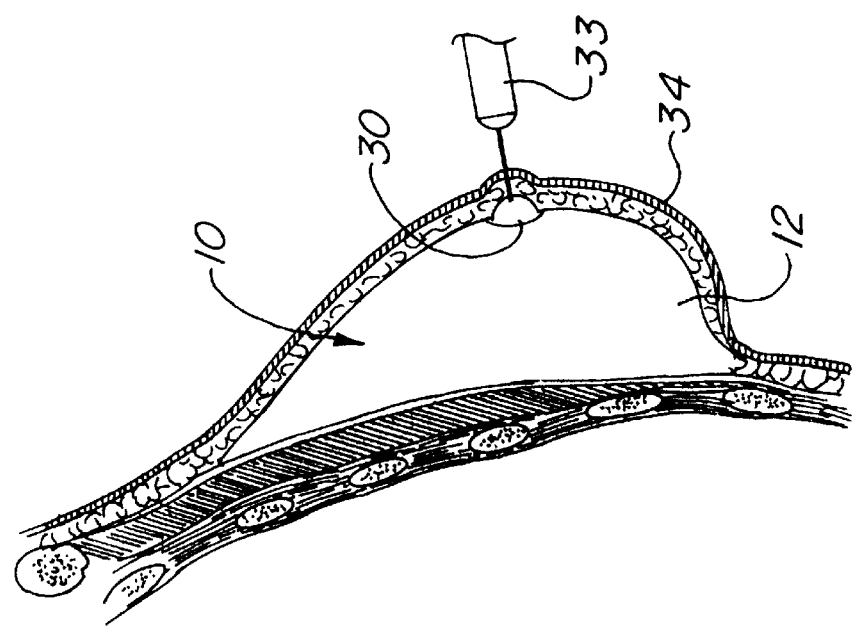
FIG. 3 is a sectional elevational view of the embodiment of FIGS. 1 and 2 showing the tissue expander fully inflated and assuming the desired shape with the overlying tissue fully expanded and conforming to the predetermined shape of the tissue expander.

With reference to FIG. 4, the tissue expanding implant 10 may be formed by the method disclosed in U.S. Pat. No. 5,376,323, which is incorporated herein by reference. A mold is prepared in the desired predetermined shape. The preferred embodiments of the present invention are described herein with regard to a breast shape. For example, when the implant 10 is to be used to replace a surgically removed breast, the implant 10 is desirably formed into a mirror image of the remaining natural breast. The device is not limited to this specific example and may be used in any situation requiring alloplastic reconstruction following ablative trauma or surgical disfiguration.

The implant is a hollow shape formed from materials having the appropriate degree of rigidity and elasticity so as to remember and regain a predetermined shape even after being collapsed and reinflated. The implant 10 may be formed from room temperature vulcanizable (RTV) silicone, such as Silastic® medical adhesive silicone Type A available from Dow Corning, which has been found to provide acceptable results in the practice of the present invention. The present invention is not limited to this material however. Any material that is bio-compatible, that is capable of being molded into a predetermined shape, and which has the mechanical properties that render the material capable of regaining the predetermined shape even after being collapsed and reinflated would be acceptable in the practice of the present invention.

In the preferred embodiment, a mold (not shown) in the shape of the anatomical feature to be replicated is injected with RTV silicone, which is allowed to vulcanize until walls 11 of vulcanized material on formed on the interior surfaces of the mold. The implant 10 is removed from the mold and the unvulcanized RTV silicone expressed from the implant 10 leaving a hollow interior 12. The implant 10 thus formed is seamless and fluid-tight. The implant 10 also replicates the predetermined shape to which the deficient anatomy is desirably to be augmented. The implant 10, while flexible, is sufficient rigid to hold the shape formed in the mold. The implant 10 is also sufficiently elastic that it can be collapsed by removing air or other filling material from the hollow interior 12 until the implant 10 is collapsed into a minimum volume similar to that shown in FIG. 1. Likewise, the implant 10 has sufficient elasticity to resume the predetermined shape upon being reinflated. The implant 10 may be formed by other methods to produce a flexible seamless shape with the requisite shape memory.

Once the implant 10 has been formed, a minimal incision is made in the patient in the area where the deficient anatomy is to be augmented. From the incision a pocket is formed under the skin of the patient. The pocket is sized to hold the implant 10, which is inserted in a collapsed deflated condition. The incision is then closed and allowed to heal.

The implant 10 is provided with a self-sealing valve 30 for periodic inflation with various types of filling material. In the preferred embodiment the filling material is air and/or a triglyceride oil, such as soybean oil or rice oil. Soybean oil (trilipid Z5) is a natural triglyceride and has been used for 40 years as an I.M. drug carrier. There is therefore a long history of the safe application of soybean oil in the human body. Saline solution may also be employed to inflate the implant 10. Soybean oil, however, has a viscosity 30 times greater than saline solution while being less dense. The combination of characteristics makes soybean oil particularly useful in the practice of the present invention since it produces a ligher weight and a more natural feel to the inflated prosthesis. Other triglycerides, such as rice oil, would also be acceptable in the practice of the present invention.

In the preferred embodiment, the self-sealing valve 30 is a latex plug 31 encapsulated with RTV silicone and incorporated into the walls 11 of the implant 10. The valve 30 is desirably formed into a protuberance 32 that can be palpated by the surgeon so that inflation can be performed with the implant 10 in place by inserting a hypodermic needle 33 through the overlying tissue 34 of the patient, through the valve 30 and into the interior 12 of the implant 10. The implant 10 is injected with the filling material at periodic intervals so that the overlying tissue 34 is gradually expanded to the appropriate extent. Since the implant 10 has previously been formed into the desired shape, the implant 10 gradually assumes the predetermined shape as it is filled. Therefore, the overlying tissue 34 likewise assumes the desired shape and predetermined volume augmenting the deficient anatomy predictably.

Unlike the prior art, the tissue expanding implant 10 does not have to be removed following the completion of tissue augmentation, and the implant 10 has a precisely predetermined shape. Although the preferred embodiment has been described with reference to augmenting and restoring deficient breast anatomy, the present invention is desirably also useful for mid-face augmentation following neoplastic surgery or trauma.

The present invention has been described with reference to certain preferred and alternative embodiments that are intended to be exemplary only and not limiting to the full scope of the present invention as set forth in the appended claims.

What is claimed is:

1. A tissue expanding shape memory implant for augmenting tissue for restoration of an anatomical feature, comprising:

a fluid-tight hollow envelope molded into a predetermined shape replicating the anatomical feature; and a self-sealing valve molded into said hollow envelope;

said fluid-tight envelope comprising walls of a material capable of being deflated for compression into a minimum volume for implantation under said tissue; said walls having sufficient stiffness and structural memory to recover said predetermined shape after being deflated and upon periodic inflation assuming said predetermined shape while gradually augmenting said tissue; and wherein said predetermined shape further comprises a protuberance capable of being palpated through the tissue of a patient and said self-sealing valve is incorporated in said protuberance.

2. The tissue expanding implant of claim 1 wherein said self-sealing valve comprises a plug of latex incorporated within said walls of said fluid-tight envelope.

3. The tissue expanding implant of claim 2 wherein said material comprising said walls comprises room temperature vulcanizable silicone.

4. The tissue expanding implant of claim 3 wherein said predetermined shape replicates a breast.

5. The tissue expanding implant of claim 4 wherein said protuberance substantially replicates a breast nipple and areola.

* * * * *